United States Patent [19]

Haast

[11] Patent Number: 4,878,597
[45] Date of Patent: Nov. 7, 1989

[54] LYOPHILIZATION CONTAINERS

[76] Inventor: William E. Haast, Miami Serpentarium Laboratories, Innovation Center University of Utah, Research Park, 419 Wakara Way, Salt Lake City, Utah 84108

[21] Appl. No.: 172,556

[22] Filed: Mar. 24, 1988

[51] Int. Cl.$^4$ ............................................. B65D 20/00
[52] U.S. Cl. ..................................... 220/404; 220/410; 422/102; 249/82; 249/153; 249/65; 249/183; 62/345
[58] Field of Search ................ 422/102; 220/404, 408, 220/410; 249/82, 149, 150, 153, 65, 179, 180, 181, 182, 183, 147; 62/340, 344, 345

[56] References Cited

U.S. PATENT DOCUMENTS

| | | | |
|---|---|---|---|
| 745,549 | 12/1903 | Woodcock | 249/82 |
| 762,972 | 6/1904 | Woodcock | 249/82 |
| 1,428,892 | 9/1922 | Latham | 249/82 |
| 1,943,384 | 1/1934 | Hall | 249/65 |
| 2,081,428 | 5/1937 | Geyer | 249/82 |
| 3,464,798 | 9/1969 | Kiltnau | 422/102 |
| 3,898,046 | 8/1975 | Ikeda et al. | 422/102 |
| 4,495,151 | 1/1985 | Ohyama et al. | 422/102 |

FOREIGN PATENT DOCUMENTS

| | | | |
|---|---|---|---|
| 406329 | 3/1922 | Fed. Rep. of Germany | 249/82 |
| 10860 | 6/1895 | United Kingdom | 249/82 |

Primary Examiner—Frankie L. Stinson
Attorney, Agent, or Firm—Kenneth E. Darnell

[57] ABSTRACT

The invention provides containers useful for freezedrying of biological and other materials which can be advantageously subjected to a lyophilization process, such materials including proteinaceous materials from which moisture is removed in order to preserve the material in a dry, shelf-stable form. The present containers allow lyophilization of the contained material with a minimum of time and energy expenditure by forming the material into a frozen shell to increase the surface area of the material and to minimize the thickness of a given quantity of material which is to be lyophilized. In a typical embodiment of the invention, a container is provided with a congruent, flexible core which is inserted into the container to force the material into the space lying between the container and the core. Expansion of the material on freezing acts to deform the flexible core rather than to break the container. The material thus frozen into a shell-like conformation within the container is then subjected to a lyophilization process after removal of the flexible core.

32 Claims, 2 Drawing Sheets

LYOPHILIZATION CONTAINERS

BACKGROUND OF THE INVENTION

1. Field of the Invention

The invention relates to containers useful for freeze-drying of biological and similar materials after formation of such a material into a frozen shell-like conformation within such containers.

2. Description of the Prior Art

Containers useful for lyophilization of biological samples are well-known in the art. Containers useful for this purpose are typically formed of glass although they may be formed of resinous materials such as are usually referred to as "plastics". Such containers typically have cylindrical sidewalls, a hemispherical bottom portion and an open end which can be capped by apparatus capable of connecting the container to valves disposed externally of a freeze drying chamber and which allow a material within the container to be subjected to vaccum conditions. Containers can also be disposed within the vacuum chambers of lyophilization apparatus such as is produced by thge Virtis Corporation, among others. Various container sizes and shapes can be adapted to use as lyophilization containers including scintillation vials, serum bottles, etc. Materials which are to be lyophilized are often simply poured into a lyophilization container such as is described above and allowed to assume the shape of the container in the manner that a liquid will assume the shape of a container. Freezing of the material within the container then forms a "slug" of frozen material which is relatively thick throughout and requires substantial time for complete lyophilization of the material. Previous techniques have addressed this problem, a common aproach being the use of "shell freezers" which comprise motor-driven rollers onto which a stoppered container containing a material which is to be freeze dried is placed. The motorized roller apparatus is placed within a freezer and activated to cause the container to rotate during the freezing process, the material then freezing into a cylindrical shell on inner surfaces of the container. A relatively thin layer of frozen material can thus be formed within the container, thereby allowing more rapid lyophilization of the material when compared to the simple formation of a frozen, relatively thicker slug within the container.

A difficulty encountered with prior shell freezers is the requirement for the relatively expensive apparatus needed for motorized rotation of the container and the requirement for placing the roller apparatus within a freezing chamber.

Another problem associated with the freezing of materials within typical lyophilization containers, particularly such containers formed of glass and similar materials, is the fact that the materials contain water which expands on freezing to exert pressure against walls of the container. These pressures can be sufficiently great to cause breakage of the container. Breakage is essentially assured in the event that the container is filled or even nearly filled with the material which is to be lyophilized.

Accordingly, a need has long existed for technology which would allow the convenient and inexpensive ability to form frozen "shells" within a lyophilization container, particularly a glass container, so that the frozen material can be frozen in a uniformly thin shell within the container without the danger of breaking the container during freezing of the material within the container. The present invention addresses this long standing need by providing lyophilization containers within which biological and similar materials can be formed into frozen shell-like conformations having substantially uniform thicknesses throughout to facilitate rapid processing of the frozen material.

SUMMARY OF THE INVENTION

The several embodiments of the lyphilization containers provided by the present invention are characterized by combination with a flexible core which is essentially congruent with a given container to allow formation of a frozen shell of material which is to be lyophilized within the containers. In a primary embodiment of the invention, a lyophilization container comprises a standard freeze-drying flask and an essentially congruent core which is sufficiently flexible to be deformable on imposition of pressure imposed over the external surface of the core. In operation, a given quantity of a material which is to be freeze dried is poured into the lyophilization flask and the core is then inserted into the flask to cause the material to fill that space lying between inner surfaces of the flask and outer surfaces of the core. The assembly is then placed in a freezer or in a freezing medium such as dry ice/acetone bath to cause the material to freeze in a shell-like conformation. As the material approaches the freezing temperature, the material expands in volume and thus exerts pressure inwardly on the resilient core, thereby deforming the core. The ability of the core to yield as the freezing material expands prevents breakage of the flask while allowing formation of a frozen shell of material which can be of a substantially constant thickness. On removal of the core, the flask is uitilized in a conventional manner either interiorly or exteriorly of a freeze drying chamber to rapidly lyophilize the shell of frozen material.

The shape of the lyophilization flask can vary to include vials, bottles, flasks, etc. of different configurations and sizes. Trays and pans can be included within the definition of containers according to the present invention. Regardless of the shape and size of the lyophilization container, a flexible core is chosen which has an outer surface essentially congruent with the inner surface of the container so that a frozen shell of substantially constant thickness throughout can be formed in order to facilitate lyophilization of the frozen material. The flexible cores of the invention can be formed in shapes which would be other than congruent with the lyophilization container, such shapes being chosen to facilitate removal of the core from the container after freezing of the material. While it is not necessary for the frozen material to have a constant thickness throughout, the lyophilization process will go to completion more rapidly whn the frozen material has a constant thickness (and a relatively thin thickness) for a given quantity of material.

Accordingly, it is a primary object of the present invention to provide lyophilization containers within which a material which is to be freeze-dried can be formed into a shell like conformation by insertion of a flexible core into the container while freezing of the material is effected.

Further objects and advantages of the invention will become more readily apparent in light of the following detailed description of the preferred embodiments.

DESCRIPTION OF THE PREFERRED EMBODIMENTS

Figure 1:
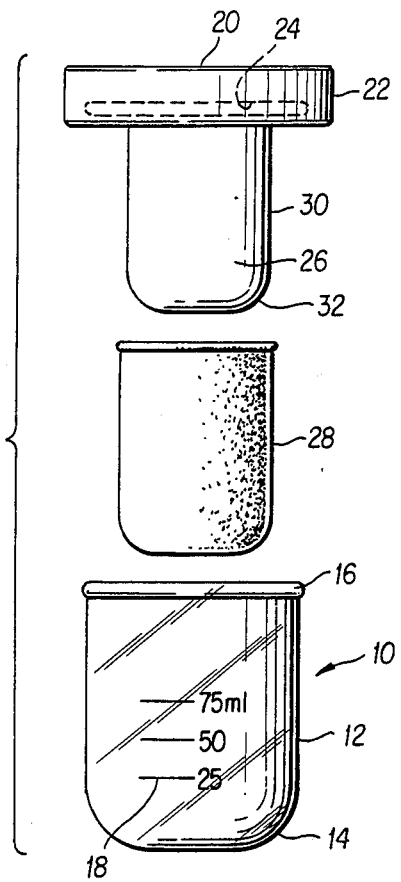
FIG. 1 is an assembly view of a lyophization flask provided with a cap and flexible core, the core having a sheath disposed over outer surfaces of the core.
Figure 2:
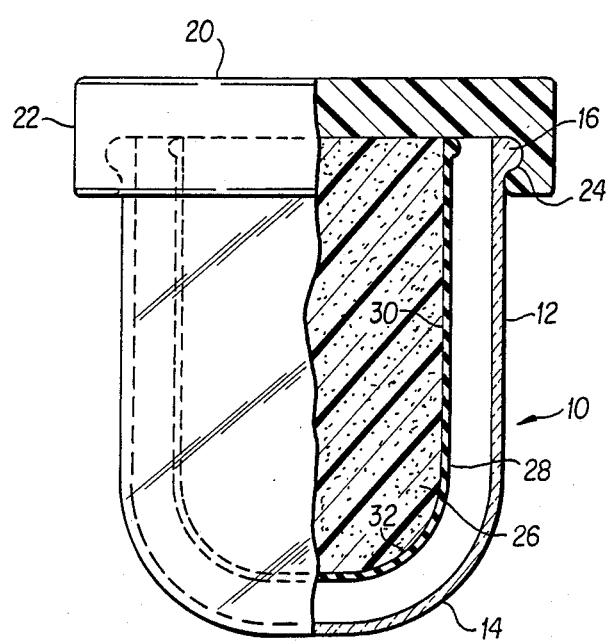
FIG. 2 is a side elevational view in section of the assembled elements shown in FIG. 1.

Referring now to the drawings and particularly to FIGS. 1 and 2, a lyophilization flask 10 is seen to have a cylindrical portion 12 closed at one end by rounded bottom 14. The open end of flask 10 is bordered by bead 16. The flask 10 is preferably formed of a borosilicate glass such as is commonly employed for the manufacture of glass flasks. The flask 10 can be formed of materials other than borosilicate or similar glasses, it only being necessary that the chosen material have the capability of withstanding the low temperatures encountered in the freezing process which will be practiced to freeze within the flask a material which is to be lyophilized while contained within the flask. The freezing process employed can vary from those temperatures encountered in a typical domestic freezer to dry ice temperatures such as would be encountered in a dry ice/acetone bath.

The flask 10 can be provided with indicia 18 to allow measurement of the quantity of liquid material which is poured into the flask prior to forming of the liquid material into a frozen, shell-like conformation within the flask 10.

A cap 20 suitable for enclosing the open end of the flask 10 is seen to have an annular lip 22 which borders and at least partially defines a race 24 into which borders and at least partially defines a race 24 into which the bead 16 of the flask 10 snaps in order to secure the cap 20 to the flask 10.

The cap 20 can be integrally formed with a core 26, this integral assembly being formed of rubber, silicone, synthetic resin or a variety of materials, the material being chosen to be flexible and yieldable so that forces directed radially inwardly against the surface of the core 26 will cause said core to yield inwardly. As an alternative construction, the cap 20 and core 26 can be formed of different materials. For example, the cap 20 can be formed of a relatively rigid "plastic" and can be attached to the core 26 by means of adhesive, heat bonding or mechanical attachment arrangements. The core 26 can be formed of a variety of fleixble materials capable of being deformed or yielding to pressures applied radially inwardly of the core. As examples, the core 26 can be formed of cross linked polyethylene foam having densities of between 1½ to 6 pounds per cubic foot and preferably wiithin a range of 1.5 to 2.5 pounds per cubic foot. Cross linked polyethylene foam useful for this application is preferably closed cell material such as that commonly employed as protective padding and for similer applications. Other polymeric materials including cross linded ethylene vinyl acetate are useful for formation of the core 26.

The core 26 can be covered by means of sheath 28, said sheath 28 being typically formed of a low friction material such as polymeric polytetrafluoroethylene. The material used to form the sheath 28 is selected for its ability to release from a frozen material formed between the sheath 28 and inner surfaces of the flask 10. As will be noted in FIG. 3, selection of a material forming the core 26 such as a closed-cell polyethylene material can provide sufficient release capability to allow the core 26 to be readily removed from the flask 10 after formation of a frozen shell of lyophilizable material within the flask 10.

Use of the sheath 28 has a further advantage of being disposable, a particularly useful feature when materials such as virsues, bacteria, or other hazardous materials from a portion of the material being processed. The sheath 28 is desirably used when the core 26 is formed of a material to which the lyophilizable material can adsorb and thereby render difficult removal of the core 26 from the lyophilizable material. The sheat 28 can be formed of a variety of nonporous, non-soluble, flexible material such as rubber, latex, silicone, polyethylene, Tygon, Teflon and the like.

The core 26 is shaped to be essentially congruent with inner surfaces of the flask 10. As can be seen in FIGS. 1 and 2, the sponge-like core 26 is shaped with a cylindrical body portion 30 with a rounded bottom 32. When the core 26 is inserted into the flask 10, outer surfaces of the core 26 (or the covering sheath 28 when a sheath is employed) are spaced from inner surfaces of the flask 10 a constant distance. While it is not absolutely necessary for the core 26 to be spaced a constant distance from the inner surfaces of the flask 10 at all locations therebetween, a constant thickness of a frozen material which is to be formed between said flask 10 and said core 26 will undergo a lyophilization process at a more uniform temporal rate. While the core 26 can be formed other than absolutely congruent with the flask 10, the formation of thicker frozen portions in the material which is to be lyophilized will result in an earlier completion of lyophilization in thinner portions of the frozen material.

Figure 3:
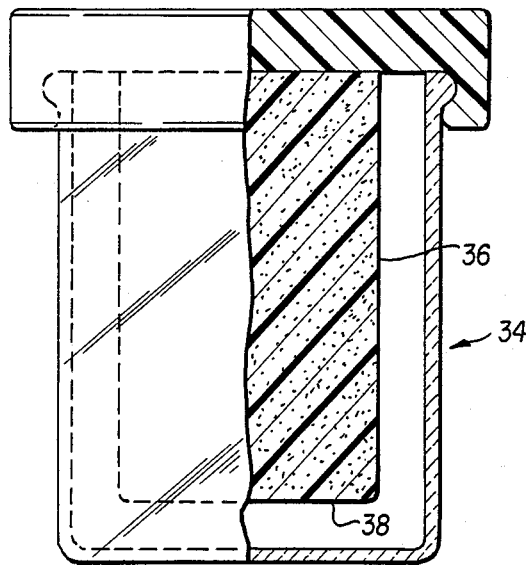
FIG. 3 is a side elevational view in section of an embodiment of the invention wherein a flexible core is not provided with a covering sheath.

The core 26 of FIGS. 1 and 2 is seen to be substantially cylindrical with a rounded end as has been noted above. However, other core configurations are possible as is seen in FIG. 3 wherein a flat-bottomed bottle 34 is provided with an essentially congruent cylindrical core 36 have a flat bottom 38. Other shapes can be utilized and the various articles of the invention can be formed of any desired and convenient size.

In use, a quantity of liquid material which is to be lyophilized is poured into the flask 10. The indicia 18 can provide graduations which allow a user to measure into the flask a quantity of material which is desired for cores of different sizes which may be used with a given flask 10. In other words, a relatively large core 26 which leaves relatively little space between said core and said flask could require as little as 25 ml of material to be poured into the flask in order to displace the material into the full volume between the core 26 and inner walls of the flask 10. Use of a large core 26 will cause a relatively thin shell of frozen material to be formed within the flask 10. Relatively smaller cores will produce relatively more thick frozen shells of material, greater quantities of lyophilizable material being poured into the flask 10 to form full frozen shells between inner walls of the flask 10 and the core.

After assembly of the cap 20 and core 26 within the flask 10, the liquid material which is to be lyophilized completely fills the space between the inner surfaces of the flask 10 and outer surfaces of the core 26 (or outer surfaces of the sheath 28). This space should be completely filled in order to form a frozen shell containing a maximum quantity of material for the thickness which has been chosen according to the size of the core 26. The assembly is then subjected to freezing temperatures in order to freeze the material which is to be lyophilized. As the material approaches the freezing temperature, the material expands since said material contains water. Expansion of the material on freezing causes a radially inwardly directed pressure to be exerted on the core 26, the core 26 yielding and deforming to accommodate the expansion. Accordingly, a frozen shell of material is formed without breakage of the flask 10 as would typically occur if the freezing material were not provided with a yieldable surface capable of accommodating expansion forces. Freezing of the material within the flask 10 can be accomplished in a standard freezer, an ultra low temperature freezer, a dry ice/acetone bath, or by subjection to sufficiently low temperatures by any suitable techniques.

After freezing of the lyophilizable material within the flask 10, the cap 20 and associated core 26 are removed from the flask 10. Use of the low-friction sheath 28 acts to facilitate release from the frozen material as noted above. On removal of the core 26 from the flask 10, the flask 10 and the contained frozen shell of lyophilizable material is connected to a freeze drying chamber or placed within such a chamber in order to lyophilize the frozen shell of material.

Figure 4:
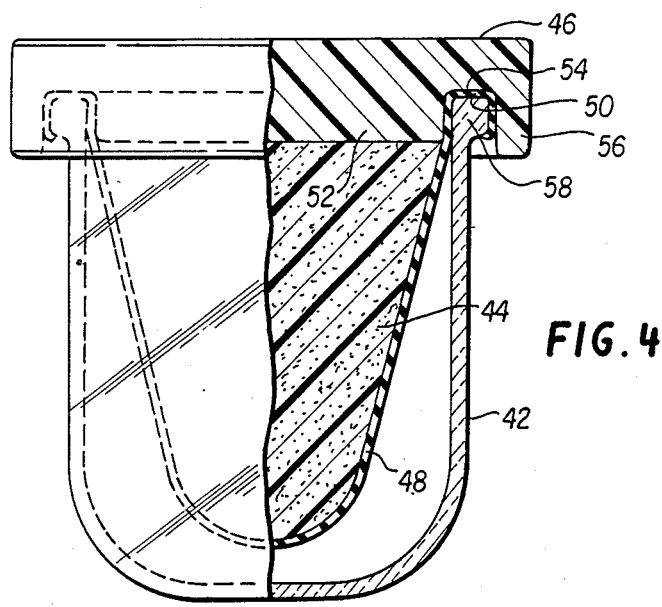
FIG. 4 is a side elevational view in section of a further embodiment of the invention wherein a sheath covering a flexible core disposed within a lyophilization container has extended portions which act to seal the container.

Referring to FIG. 4, a flask 42 essentially identical to the flask 10 acts in concert with core 44 and associated cap 46 in a manner essentially identical to that described relative to the embodiments of FIGS. 1 through 3. The core 44 is tapered to further facilitate release of the core from the frozen material. The taper of the core 44 produces a shell of frozen material which will not have a constant thickness throughout. Lyophilization will therefore not be complete at essentially the same time at all locations of the frozen shell. The taper of the core 44 renders use of a sheath such as the sheath 28 less necessary unless it is desired to dispose of the sheath after use such as would be desirable when hazardous materials are to be lyophilized. Further advantages are provided by sheath 48 which has annular extended portions 50. THe portions 50 conform to inner surfaces of the cap 46 to form a sealing membrane. The cap 46 is provided with a plug portion 52 which extends into the open end of the flask 42 and defines an annular recess 54 in concert with external flange 56 of the cap 46. The open end of the flask 42 extends into the recess 54 with bead 58 of said flask 42 acting in concert with the protions 50 of the sheath 48 to seal the assembly. The assembly thus formed prevents loss of lyophilizable material regardless of the angle at which the assembly is disposed during handling or subsequent freezing. The core 44 can be hollow to allow insertion into a bottle having a relatively small neck.

Figure 5:
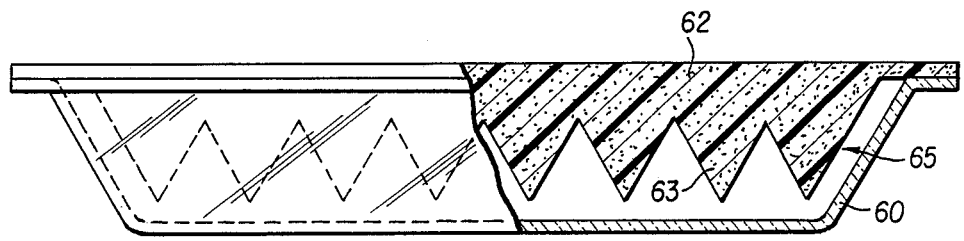
FIG. 5 is a side elevational view in section of a tray-like embodiment of the invention; and, FIG. 6 is a side elevational view in section of an embodiment of the invention wherein the flexbile core essentially comprises an inflatable bladder.

Referring now to FIG. 5, a tray 60 is seen to be used in concert with a core 62 which is shaped to have corrugations 63 which act to increase the surface areas of frozen material formed between the corrugations 63 and the inner surfaces of the try 60. Use of the tray 60 and the core 62 allows formation of a frozen shell of lyophilizable material in essentially the same manner as is described above relative to the flask 10 inter alia. The core 62 is formed of a resilient material having the characteristics referred to above relative to the core 26 inter alia. The core 62 is tapered at 65 to facilitate release from the frozen shell. The various core structures described herein can be similarly tapered. The core 62 can also be formed into a flat lower surface rather than with the corrugations 63, thereby producing frozen material having a more uniform thickenss throughout.

Other patterns, such as a waffle iron pattern, could be used in place of the corrugations 63 in order to form patterns in the frozen material which increase the surface of the frozen material.

Figure 6:
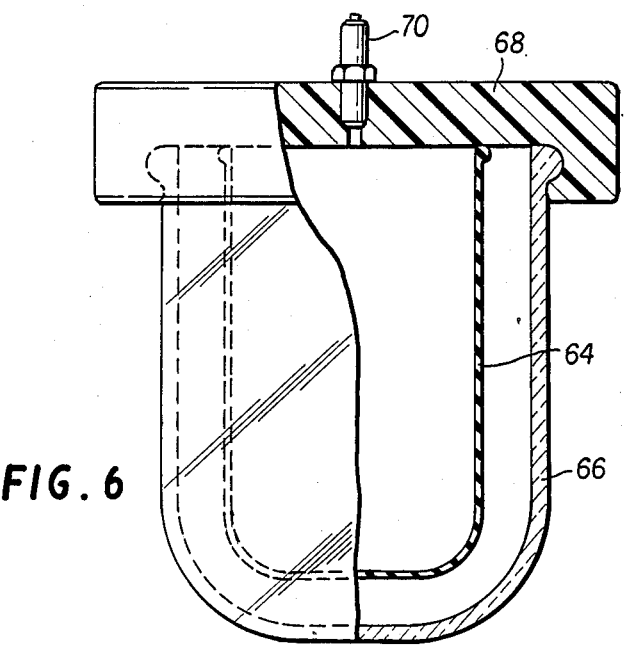

In FIG. 6, an inflatable core 64 is seen to be disposed within flask 66, the core 64 being joined to a cap 68. The assembly of FIG. 6 can be utilized in essentially the same manner as the embodiments of FIGS. 1 through 4, the inflatable core 64 accommodating expansion of a lyophilizable material which is frozen within the space between the core 64 and inner walls of the flask 66. The core 64 can be inflated through a conventional valve 70 disposed in the cap 68. Inflation can be accomplished either before or after insertion of the core into the flask. The core is attached to the cap in a manner such as is described above.

Although the invention has been described relative to the several embodiments thereof shown explicitly in the drawings and described above, it is to be understood that the invention can be practiced other than as described and shown without departing from the scope of the invention. Accordingly, the invention is to be defined by the scope of the appended claims.

What is claimed is:

1. Lyophilization apparatus, comprising:
   container means for receiving a lyophilizable material;
   core means insertable into the container means for displacing the lyophilizable material into that space between opposed surfaces of the container means and core means, the core mean being deformable on freezing of the lyophilizable material to form a frozen shell of lyophilizable material; and,
   sheath means receivable over the core means for facilitating release of the core means from the frozen shell of lyophilizable material.

2. The apparatus of claim 1 and further comprising:
   cap means attached to the core means for closing the container means.

3. The apparatus of claim 1 wherein outer surfaces of the core means are congruent with inner surfaces of the container means.

4. The apparatus of claim 1 wherein the core means is tapered in conformation.

5. The apparatus of claim 1 wherein the core means is formed of a compressible material which is continuous throughout said core means.

6. Lyophilization apparatus, comprising:
   container means for receiving a lyophilizable material;
   core means insertable into the container means for displacing the lyophilizable material into that space between opposed surfaces of the container means and core means, the core means being deformable on freezing of the lyophilizable material to form a frozen shell of lyophilizable material;
cap means attached to the core means for closing the container means; and
sheath means receivable over the core means for facilitating release of the core means from the frozen shell of lyophilizable material.

7. The apparatus of claim 6 wherein the core means is tapered in conformation.

8. The apparatus of claim 6 wherein the core means is hollow.

9. The apparatus of claim 6 wherein the core means is inflatable.

10. The apparatus of claim 6 wherein outer surfaces of the core means are congruent with inner surfaces of the container means.

11. The apparatus of claim 6 wherein the core means is formed of a compressible material which is continuous throughout said core means.

12. Lyophilization apparatus, comprising:
container means for receiving a lyophilizable material;
core means insertable into the container means for displacing the lyophilizable material into that space between opposed surfaces of the container means and core means, outer surfaces of the core means being congruent with inner surfaces of the container means, the core means being deformable on freezing of the lyophilizable material to form a frozen shell of lyophilizable material; and,
sheath means receivable over the core means for facilitating release of the core means from the frozen shell of lyophilizable material.

13. The apparatus of claim 12 wherein the core means is hollow.

14. The apparatus of claim 12 wherein the core means is inflatable.

15. The apparatus of claim 12 and further comprising: cap means attached to the core means for closing the container means.

16. The apparatus of claim 12 wherein the core means is formed of a compressible material which is continuous throughout said core means.

17. Apparatus for forming a lyophilizable material into a shell-like conformation wherein the material can be frozen in said conformation and wherein the surface area of the material frozen within the apparatus is increased without damage to the apparatus which could be occasioned by expansion of the lyophilizable material on freezing thereof, comprising:
container means for receiving a lyophilizable material;
deformable core means insertable into the container means for displacing the lyophilizable material into that space between opposed surfaces of the container means and core means, the core means being deformable on freezing of the lyophilizable material to form a frozen shell of lyophilizable material; and,
sheath means receivable over the core means for facilitating release of the core means from the frozen shell of lyophilizable material.

18. The apparatus of claim 17 wherein the core means is tapered in conformation.

19. The apparatus of claim 17 wherein the core means is hollow.

20. The apparatus of claim 17 wherein the core means is inflatable.

21. The apparatus of claim 17 wherein the core means is formed of a compressible material which is continuous thoroughut said core means.

22. The apparatus of claim 21 wherein the core means is formed of a compressible foam material.

23. The apparatus of claim 17 and further comprising: cap means attached to the core means for closing the container means.

24. The apparatus of claim 17 wherein outer surfaces of the core means are congruent with inner surfaces of the container means.

25. Apparatus for forming a lyophilizable material into a shell-like conformation wherein the material can be frozen in said conformation and wherein the surface area of the material frozen within the apparatus is increased without damage to the apparatus which could be occasioned by expansion of the lyophilizable material on freezing thereof, comprising:
container means for receiving a lyophilizable material; and,
deformable core means insertable into the container means for displacing the lyophilizable material into that space between opposed surfaces of the container means and core means, the core means being formed of a compressible material which is continuous throughout said core means, the core means being deformable on freezing of the lyophilizable material to form a frozen shell of lyophilizable material.

26. The apparatus of claim 25 wherein the core means is formed of a compressible foam material.

27. the apparatus of claim 25 and further comprising: sheath means receivable over the core means for facilitating release of the core means from the frozen shell of lyophilizable material.

28. The apparatus of claim 25 and further comprising: cap means attached to the core means for closing the container means.

29. The apparatus of claim 25 wherein outer surfaces of the core means are congruent with inner surfaces of the container means.

30. The apparatus of claim 26 wherein the core means is tapered in conformation.

31. The apparatus of claim 25 wherein the core means has a corrugated pattern formed in a surface facing a surface of the container means to increase the surface area of frozen material formed between the core means and the container means.

32. A method for forming a lyophilizable material into a frozen shell to thereby increase the surface area of the lyophilizable material and to prevent damage to a container within which the lyophilizable material is frozen, comprising the steps of:
placing a quantity of a lyophilizable material into a container within which the lyophilizable material is to be frozen;
inserting a deformable core element into the container to displace at least a portion of the lyophilizable material into that space between opposed surfaces of the container and the core element;
subjecting the assembly of container and core element to conditions sufficient to freeze the lyophilizable material, the core element being deformed on freezing of the lyophilizable material to prevent damage to the container;
removing the core element from the container while maintaining the lyophilizable material is a frozen condition; and,
subjecting the frozen lyophilizable material to conditions sufficient to lyophilize said material.

* * * * *